United States Patent [19]
Lilienfeld

[11] Patent Number: 5,319,575
[45] Date of Patent: Jun. 7, 1994

[54] SYSTEM AND METHOD FOR DETERMINING AND OUTPUTTING AIRBORNE PARTICLE CONCENTRATION

[75] Inventor: Pedro Lilienfeld, Lexington, Mass.
[73] Assignee: TRC Companies, Inc., East Hartford, Conn.
[21] Appl. No.: 28,785
[22] Filed: Mar. 10, 1993

Related U.S. Application Data
[63] Continuation of Ser. No. 644,209, Jan. 22, 1991, abandoned.

[51] Int. Cl.⁵ ............................................. G01N 21/84
[52] U.S. Cl. .................................................... 364/555
[58] Field of Search ............... 356/335, 336, 337, 338; 364/555

[56] References Cited

U.S. PATENT DOCUMENTS 3,692,412  9/1972  Chubb ................................. 356/103
4,940,327  7/1990  Lilienfeld ........................... 265/338

OTHER PUBLICATIONS

"Rotational Electrodynamics of Airborne Fibers"; Lilienfeld; J. Aerosol Sci., vol. 16, No. 4, pp. 315–322 (1985).
"Light Scattering From Oscillating Fibers At Normal Incidence"; Lilienfeld; J. Aerosol Sci., vol. 18, No. 4, pp. 389–400 (1987).
MIE Application Note, No. 4–A; Jan. 24, 1990.
MIE Fiber Monitor Model FM-7400 User's Manual; Jul. 1991.
"An Introduction to Scientific Research"; Wilson; Section 9.2; pp. 236–237. (no date).

Primary Examiner—Edward R. Cosimano
Attorney, Agent, or Firm—Hale and Dorr

[57] ABSTRACT

A system and method for determining airborne particle concentrations. When in a fixed time period mode of operation, the system determines actual airborne particle concentration when a normal particle count is detected, and determines an "upper limit" particle concentration based on Poisson statistics when a low particle count is detected. In a fixed precision mode of operation, the system determines in advance the number of particles needed to be detected to achieve an airborne particle concentration measurement having a precision equivalent to a user selected fixed precision, and prints out airborne concentration measurements only when such measurements have the user selected fixed precision.

15 Claims, 5 Drawing Sheets

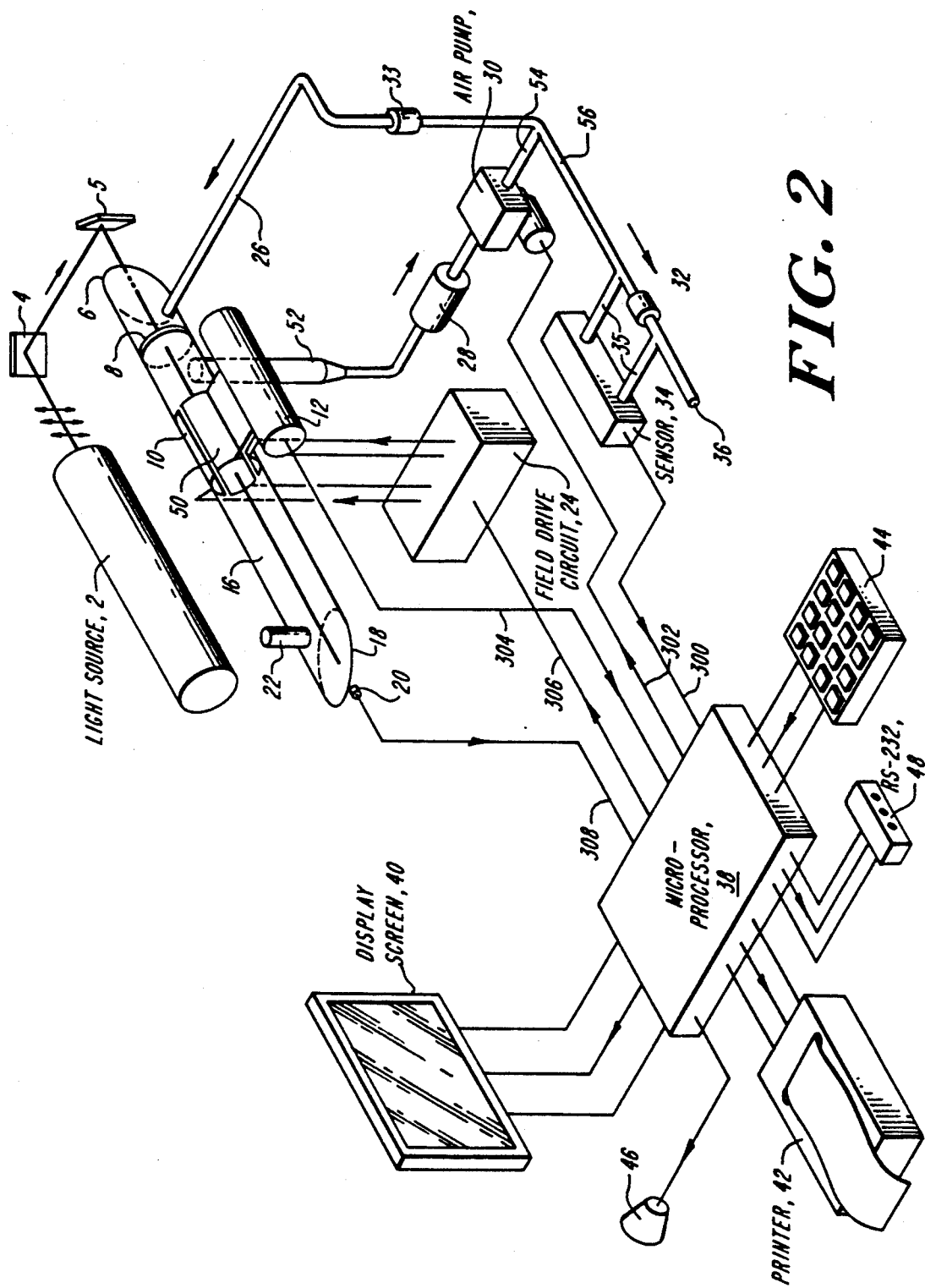

SYSTEM AND METHOD FOR DETERMINING AND OUTPUTTING AIRBORNE PARTICLE CONCENTRATION

This invention relates to a system and method in an particle aerosol monitor for determining and outputting airborne particle concentrations. This application is a continuation of U.S. Ser. No. 07/644,209, filed Jan. 22, 1991 and now abandoned.

BACKGROUND OF THE INVENTION

Currently, the typical method for monitoring the presence and concentration of airborne particles is a process wherein the air is continuously sampled and particles are detected by means of light scattering. This method is incorporated in most aerosol particle monitors which monitor the environment by Continuously illuminating air samples. The pattern of light scattered by any particle present in the air sample makes it possible to identify and count each particle on a real time basis. Airborne particle concentration (C) is then determined by dividing the number of particles counted (p) by the elapsed sampling time (t) multiplied by the detection flow rate ($Q_d$) of the air sample through the monitor. Thus, by equation:

$$C = \frac{p}{(Q_d * t)}$$

Prior art particle monitors then display the particle count and related particle concentration in real time on a display means, usually a light emitting diode ("LED") or a liquid crystal display ("LCD") screen. Additionally, these devices allow the particle count and concentration to be continually outputted to a strip chart recorder, data logger and/or telemetry system.

Prior art real time particle monitors are able to determine an environment's actual airborne particle concentration with statistical meaning when the concentration is relatively high, that is, when the total particle count (p) is sufficiently large for a particular sampling period (t) or if the sampling period is made sufficiently long. Problems arise when these prior art devices attempt to determine an environment's actual particle concentration when the concentration is very low, that is, when the total particle count (p) is very low for a particular sampling period (t). Specifically, a particle count of zero during a test sampling period is not necessarily equivalent to zero particle concentration. Similarly, a very low particle count, for example a count of 1, 2, or 3, will result in a particle concentration measurement with an implied large degree of uncertainty. As a result, when these devices are used in environments having a low airborne particle concentration, such as in clean rooms or when monitoring fibers in ambient outside air, they must be operated for long periods of time to achieve a statistically meaningful determination of particle concentration. For example, if an environment has an expected airborne particle concentration of 0.1 p/cc (particles per cubic centimeter), a particle monitor sampling air with a detection flow rate of 10 cc/min must be operated for approximately 100 minutes to determine the environment's actual particle concentration with adequate precision. When a particle monitor is used in an environment having an even lower particle concentration, the required operating time increases correspondingly, Accordingly, it would be desirable to be able to determine over shorter periods of time an "upper limit" particle concentration with a significant degree of confidence. That is, to be able to state that the probable airborne particle concentration is below a certain value. Additionally, it would be desirable to be able to determine the required sampling time at a zero or low particle count to state with a significant degree of confidence that the actual particle concentration is below a certain value.

Prior art particle monitors are also unable to determine and printout particle concentrations having a constant, preferably user selected, fixed measurement precision. The inability to determine and printout particle concentrations having a selected measurement precision (i.e. to monitor an environment in a fixed precision mode) complicates particle monitoring when an environment's expected particle concentration is not known. In this situation, a required sampling time period (t) for a selected precision must first be determined. Then, the monitor must be operated for the predetermined time period to achieve an actual airborne particle concentration within the selected precision level. For example, to use a particle monitor in an environment where the expected particle concentration is not known, the user must first operate the monitor continuously to determine the time required to count 20 particles ($t_{20}$). Then, to determine the required total sampling time (t) to achieve a particle concentration within a selected constant precision (PR) (at a confidence level of 95%), the user must solve the following equation:

$$t = t_{20} \left( \frac{44.72}{PR} \right)^2$$

Finally, the user must operate the monitor for t minutes to determine the actual airborne particle concentration within the selected precision P (at a confidence level of 95%). Therefore, if it took 40 minutes to count 20 particles ($t_{20}=40$), and a user selected a measurement precision of ±20% (PR=20), the required total sampling time (t) is 200 minutes (200=40 $(44.72/20)^2$). The user must then operate the monitor for 200 minutes to determine the actual airborne particle concentration with a precision of 20% at a confidence level of 95%.

The inability to output airborne particle concentrations in a fixed precision mode also prevents the user from obtaining more frequent concentration outputs when the airborne particle concentration increases, a situation where such information is most needed, or from obtaining concentration outputs having only a selected precision.

OBJECTS OF THE INVENTION

Therefore, it is an object of the present invention to provide a system and method to determine an upper limit airborne particle concentration with statistical significance.

Another object of the present invention is to provide a system and method to determine an upper limit airborne particle concentration with statistical significance when a zero or low airborne particle count is encountered during a fixed sampling time period.

Another object of the present invention is to provide a system and method to determine the required sampling time to state with significant degree of confidence that the actual airborne particle concentration is below a certain value.

Another object of the present invention is to provide a system and method to determine the required sampling time at a zero or low airborne particle count to state with a significant degree of confidence that the actual airborne particle concentration is below a certain value.

Another object of the present invention is to provide a system and method to determine an actual airborne particle concentration having a user selected fixed precision to simplify particle monitoring when the expected particle concentration is not known.

Another object of the present invention is to provide a system and method to frequently output actual airborne particle concentrations having a user selected fixed precision whenever such concentrations increase.

Another object of the present invention is to provide a system and method to output airborne particle concentrations only when such concentrations have a user selected fixed precision.

Objects and advantages of the invention are set forth in part herein and in part will be obvious therefrom, or may be learned by practice with the invention, the same being realized and attained by means of the instrumentalities and combinations pointed out in the appended claims. The invention consists of the novel parts, constructions, arrangements combinations, steps and improvements herein shown and described.

SUMMARY OF THE INVENTION

The preferred embodiment for a system and method for determining and printing airborne particle concentration includes, inter alia, a real time particle monitor having, a particle counting means, a display means, a keyboard means, a printout and/or other output means, and a processing means to control the interaction of the various electronic components and to perform necessary calculations.

The system allows a user to select a fixed time period or a fixed precision mode of operation for the particle monitor. When the system is in the fixed time period mode and a normal particle count is detected, the system advances to a routine to determine the actual airborne particle concentration and the associated precision of that determination in a normal manner. When a low particle count is detected, the system advances to a low particle count routine to determine an "upper limit" particle concentration based on Poisson statistics. At the expiration of the user selected fixed time period, the system prints out either the appropriate upper limit particle concentration or the actual particle concentration and associated precision. Operation in the fixed time period mode is preferred if (i) hard copy information is to be correlated to specific events, (ii) the particle concentration is expected to be fairly constant over a period of time, or (iii) a specific number of determinations are required within a work shift.

Alternatively, when the system is in the fixed precision mode, the system prints out airborne particle concentration measurements only when such measurements have a user selected fixed precision. In this mode, the system determines in advance the number of particles needed to be detected to achieve an airborne particle concentration measurement having a precision equivalent to the user selected fixed precision. The system then waits until the actual particle count is equivalent to the required particle count before printing the airborne particle concentration. Operation in the fixed precision mode is preferred if (i) no prior information concerning the expected particle concentration is available, (ii) the airborne particle concentration is expected to change, or (iii) only particular statistical results are need.

The printed values for airborne particle concentration and precision for either the fixed time period or fixed precision modes represent the current airborne concentration since the last printout. The system also displays on a LCD screen the total particle count since commencement of monitoring as well as the time weighted average airborne particle concentration and precision, or upper limit airborne particle concentration, since commencement of monitoring. The combination of LCD and printout data presentation provides an all encompassing and versatile presentation of information on airborne particle concentration.

As will be readily apparent to those skilled in the art, the system and method of the present invention is applicable to any type of particle monitoring including the specific field of fiber monitoring.

BRIEF DESCRIPTION OF THE DRAWINGS

The accompanying drawings, referred to herein and constituting a part hereof, illustrate preferred embodiments of the system and method of the present invention, and together with the description, serve to explain the principles of the invention.

FIG. 2 is a schematic illustration of a fiber monitor in accordance with the present invention.

DETAILED DESCRIPTION OF THE DRAWINGS AND PREFERRED EMBODIMENTS

The following is a detailed description of the drawings and preferred embodiments of the present invention for a system and method for determining airborne particle concentration. The preferred embodiment for a system and method for determining and printing airborne includes, inter alia, a real time particle monitor having a particle counting means, a liquid crystal display screen, a keyboard, a printer and/or other output means and a programmable microprocessor to control the interaction of the various electronic components and to perform necessary calculations.

The system and method has two modes of printing: fixed time period and fixed precision. In the fixed time period mode, the system and method determines over a fixed time period the actual airborne particle concentration for a normal particle count or an "upper limit" particle concentration for a low particle count. At the end of the fixed time period the system and method prints the resulting actual or upper limit particle concentration. Operation in the fixed time period mode is preferred if (i) hard copy information is to be correlated to specific events, (ii) the particle concentration is expected to be fairly constant over a period of time, or (iii) a specific number of determinations are required within a work shift.

In the fixed precision mode, the system and method determines the particle concentration and prints out same only when the determination has a precision equivalent to a user selected fixed precision. Operation in the fixed precision mode is preferred if (i) no prior information concerning the expected particle concentration is available, (ii) the airborne particle concentration is expected to increase, or (iii) only particular statistical results are needed.

The printed values for airborne particle concentration and precision for either the fixed time period or fixed precision mode represent the current airborne concentration and precision since the last printout. The system also displays on the LCD screen the total particle count since commencement of monitoring as well as the time weighted average airborne particle concentration, or the upper limit particle concentration, since commencement of monitoring. The combination of LCD and printout data presentation provides an all encompassing and versatile presentation of information on airborne particle concentration.

As will be readily apparent to those skilled in the art, the below described system and method for determining and printing airborne particle concentration is applicable to all particle monitors including the specific field of fiber monitoring.

Figure 1:
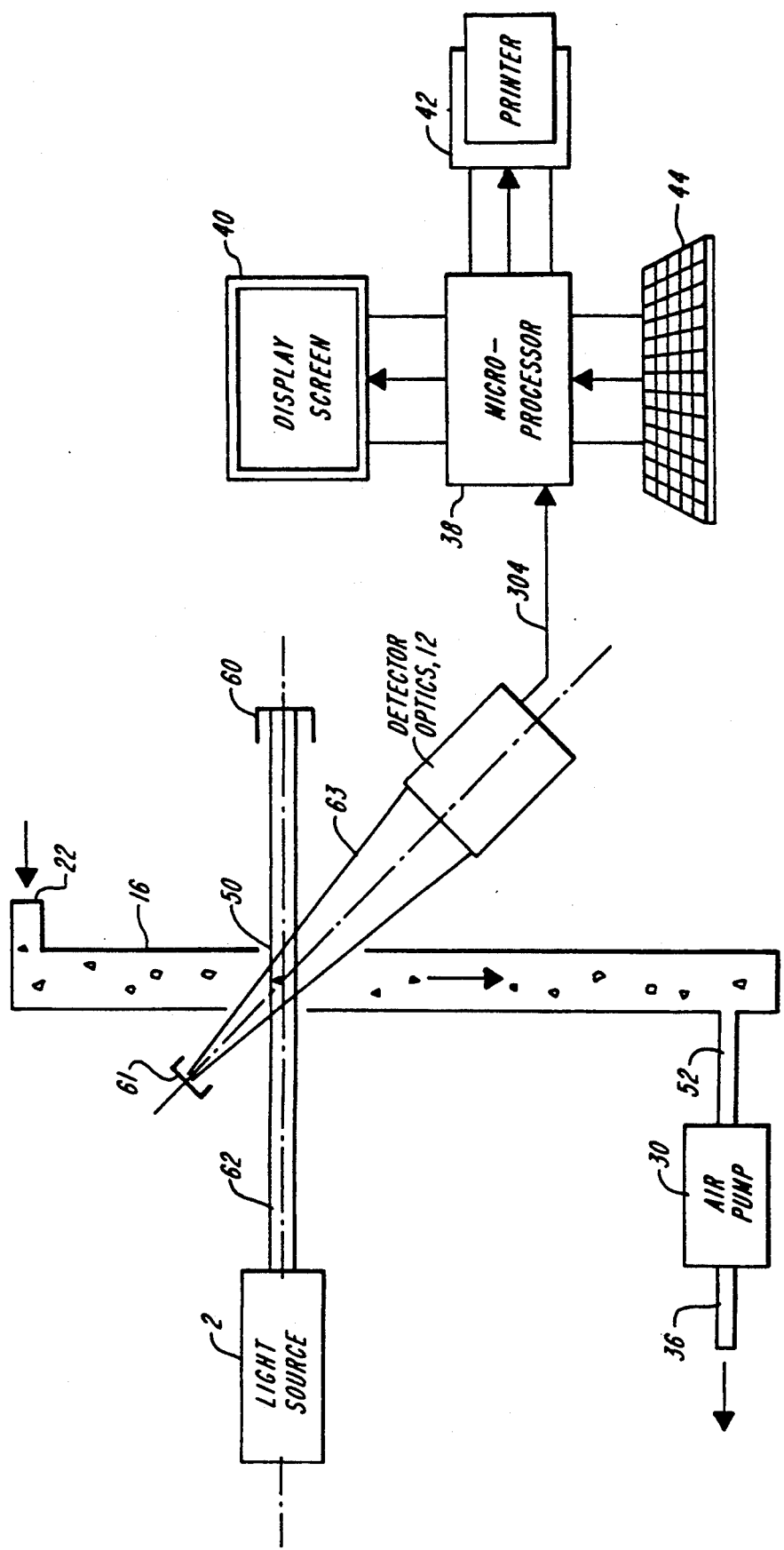
FIG. 1 is a schematic illustration of a general particle monitor in accordance with the present invention.

FIG. 1 shows a general schematic view of the preferred system and method in accordance with the present invention as used in a particle monitor.

As shown in FIG. 1, an air sample is obtained through a sampling inlet 22, preferably an omnidirectional slit-type entry port. Depending upon sampling requirements, other types of inlets, such as a straight pipe inlet, may be appropriate. The sample air flows into one end of a flow tube 16 and then flows towards the downstream end. An exhaust duct 52 is connected to flow tube 16 downstream from sensing zone 50. The air then leaves the flow tube 16, enters exhaust duct 52, and is vented through vent tube 36 by an air pump 30. The flow rate of the particle monitor system can be varied, e.g., from as low as 1 cubic centimeter per minute (1 cc/min) to as high as 1 cubic feet per minute (1 cfm). Additionally, the actual flow rate of the air detected ($Q_d$) can vary correspondingly.

A light source 2 is used to illuminate any particles present in sensing zone 50. Detection optics 12, preferably a photomultiplier tube, is used to detect the characteristic light scattering pulses of the particles illuminated by light source 2 within the sensing zone 50 defined by the intersection of light beam 62 and detector field of view 63. Light traps 60 and 61 are used to prevent light from reflecting back into the sensing zone 50. The detection optics 12 continuously signals to the microprocessor 38 via signal line 304 for each particle detected. Microprocessor 38 is used to maintain the total particle count over an elapsed time.

As is well known to those skilled in the art, particle counting and fiber counting differ mainly in their sensing techniques. Whereas particles monitors need only to illuminate each airborne particle to detect same, fiber monitors are required, in addition to such illumination, to align and oscillate each fiber to distinguish these fibers from other particles. As will become readily apparent to those skilled in the art, the present invention's system and method for determining and printing airborne particle concentration is applicative to both types of monitoring.

Referring now to FIG. 2, a schematic illustration of a fiber monitor incorporating the present invention is disclosed. The numbering of the common elements between the particle monitor and fiber monitor are the same for simplicity of discussion.

As shown in FIG. 2, an air sample is obtained through a sampling inlet 22, preferably an omnidirectional slit-type entry port. Depending upon sampling requirements, other types of inlets, such as a straight pipe inlet, may be appropriate. The sample air flows into one end of a flow tube 16 and then flows towards the downstream end. A sufficient distance is provided between the upstream inlet 22 and downstream sensing zone 50 to ensure stable laminar flow during the sensing zone 50. A side duct 52 is connected to flow tube 16 downstream from sensing zone 50. The air then leaves the flow tube 16, enters side duct 52, and passes through an in-line particle filter 28 connected to an air pump 30. It is contemplated that filter 28 may be analyzed by standard chemical and/or microscopic methods to confirm the realtime fiber count obtained with the present invention. As shown, the filtered pump exhaust S4 is split into two branches: a small secondary fraction (approximately 10%) 15 recirculated back to flow tube 16 through the clean air feed line 26, and a main exhaust branch 56 which includes a flow restrictor 32 and out through exhaust 36. The recirculated air through feed line 26 is regulated by another flow restrictor 33 and enters the downstream end of flow tube 16 behind laser beam aperture 8 so as to prevent dust deposition on the internal surface of window 6. A flow rate sensor 34 having a differential pressure transducer is connected to the main exhaust branch by two flow rate side ducts 35, one before the flow restrictor 32 and the other after. The pressure drop developed across flow restrictor 32 is sensed by the differential pressure transducer whose output voltage is monitored by a programmable microprocessor 38 through transducer voltage measure line 300, and used for automatic control of the flow rate of pump 30 through pump flow rate control line 302. The flow rate of the fiber monitor system is preferably maintained at a constant value of 2 liters per minute (2 lpm) for computing fiber concentration. It has been found that with an overall air flow rate of 2 lpm through the monitor the actual flow rate of the air detected ($Q_d$) is 10 cc/mm, or approximately 1/200 of the overall air flow through the monitor.

Fiber alignment and oscillation in sensing zone 50 are accomplished through an electric field quadrupole 10 which is driven by an electric field drive circuit 24 and controlled by the microprocessor 38 via control line 306. This type of time varying electric field quadrupole is illustrated and described in "Rotational Electrodynamics of Airborne Fibers", Lilienfeld, J. Aerosol Sci., Vol. 16, No. 4, p. 315 at pp. 319-321 (1985) In general, four quadrupole elements are provided and a high voltage d.c. field is applied across the upper quadrupole member pair and the lower quadrupole member pair to vertically align the fibers in the stream. An a.c. voltage is applied across the left side quadrupole member pair and the right side quadrupole member pair. The Superimposed fields result in a field intensity at the center of the quadrupole of between 3,000 to 3,400 volts per centimeter, with fibers in the field aligned vertically when the a.c. component passes through zero. As the a.c. component increases in the positive or negative direction, fibers in the sample are rotated out of vertical alignment and periodically oscillated. Because light scattered from perpendicularly illuminated fibers is sharply concentrated at and near the plane normal to the fiber axis, the foregoing electric field, as included in the Fibrous Aerosol Monitor ("FAM-1") available from Monitoring Instruments for the Environment ("MIE"), Bedford, Massachusetts, makes it possible to observe and count the concentration of fibers present in a given sample. See "Light Scattering From Oscillating Fibers At Normal Incidence", Lilienfeld, J. Aerosol Sci., Vol. 18, No. 4, p. 389 (1987).

A polarized helium-neon laser 2 operating at a preferred wavelength of 632.8nm is used as a light source to provide an illumination beam which is centered in the flow tube 16 by means of two locking mirrors 4 and 5. The laser beam intensity and alignment are monitored by a laser beam alignment detector 20 which receives a fraction of the beam, which is highly attenuated by a special non-reflecting Brewster-angle absorber window 18. The laser beam alignment detector 20 is controlled by the microprocessor 38 via control line 308.

A photomultiplier tube 12 detects the characteristic light scattering pulses resulting from the rapid oscillation (preferably 400 oscillations per second) of the aligned fibers passing along the laser beam. The photomultiplier then continuously signals to the microprocessor 38 via signal line 304 for each fiber detected. Microprocessor 38 is used to maintain the total fiber count over an elapsed time period.

In both the particle and fiber monitors of FIGS. 1 and 2 all control signals are generated and processed by means of the programmable microprocessor 38. All user controls, programming, and commands are selected and entered through the front panel keyboard 44. All data, statuses, instructions, menus, and diagnostic readings are displayed on a liquid crystal display (LCD) screen 40, and hard copy data and early warning messages are generated by printer 42. An audible alarm 46, not shown in FIG. 1, is activated whenever user selected particle concentration levels are exceeded. A standard RS-232 digital port 48, not shown in FIG. 1, is provided for remote data transmission and control and/or further computer data processing. In addition, an analog output signal can be made available for strip chart recordings.

The programmable microprocessor 38 functions as a programmable data processing means to control the interaction of the various electronic components used in the monitor and to perform necessary calculations. As will be readily apparent to those skilled in the art, the microprocessor of the type used in the present invention can be programmed to control the various electronic components in numerous ways to achieve a system and method for determining and printing particle concentration in accordance with the present invention. Accordingly, the particular processing steps as described below are directed to a preferred embodiment of the invention and are by no means intended to limit the scope of the claims.

Figure 3A:
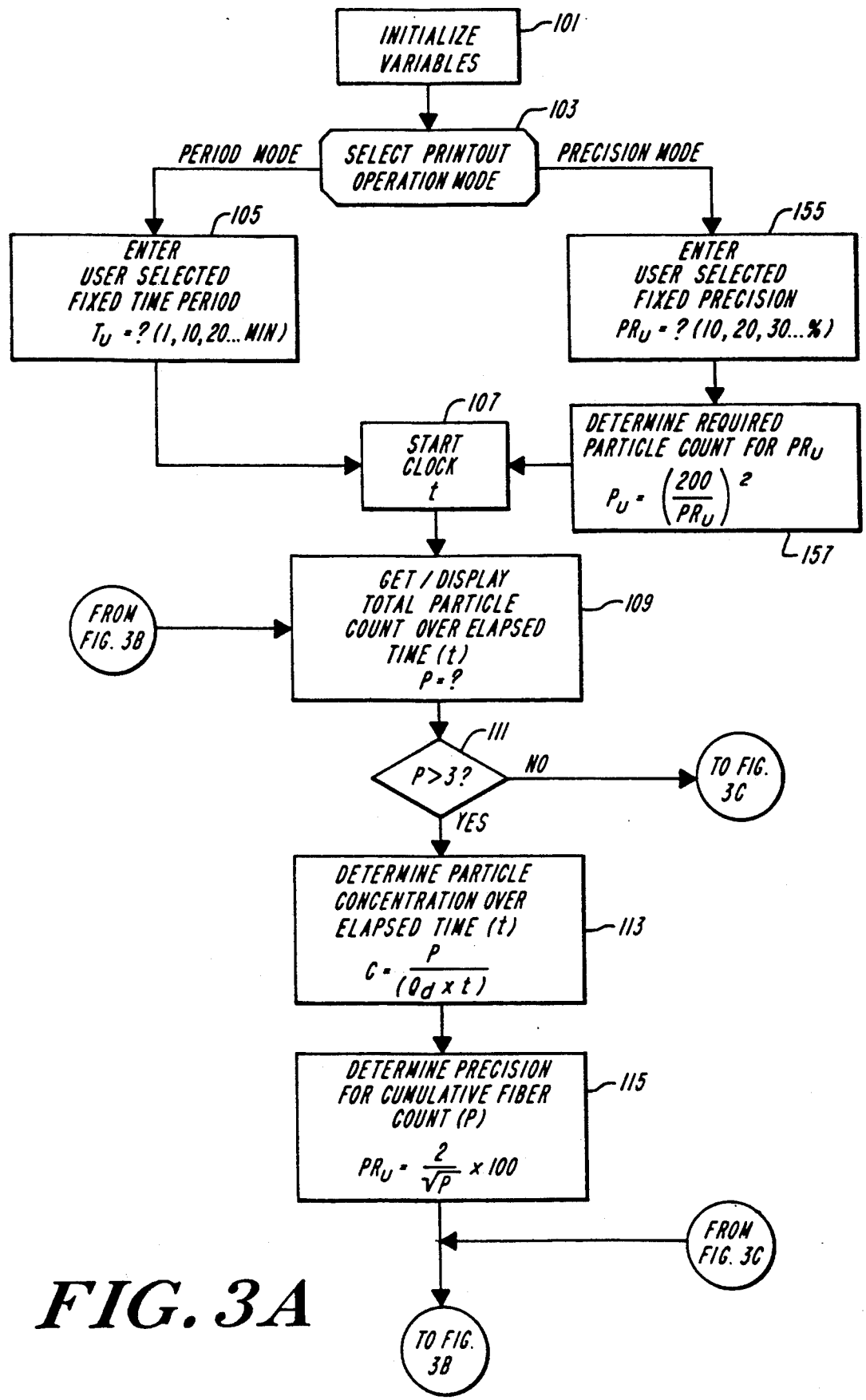
FIGS. 3A–3C is a flow chart illustrating the processing steps for determining airborne particle count and concentration and displaying and outputting same in a fixed time period or fixed precision mode.
Figure 3B:
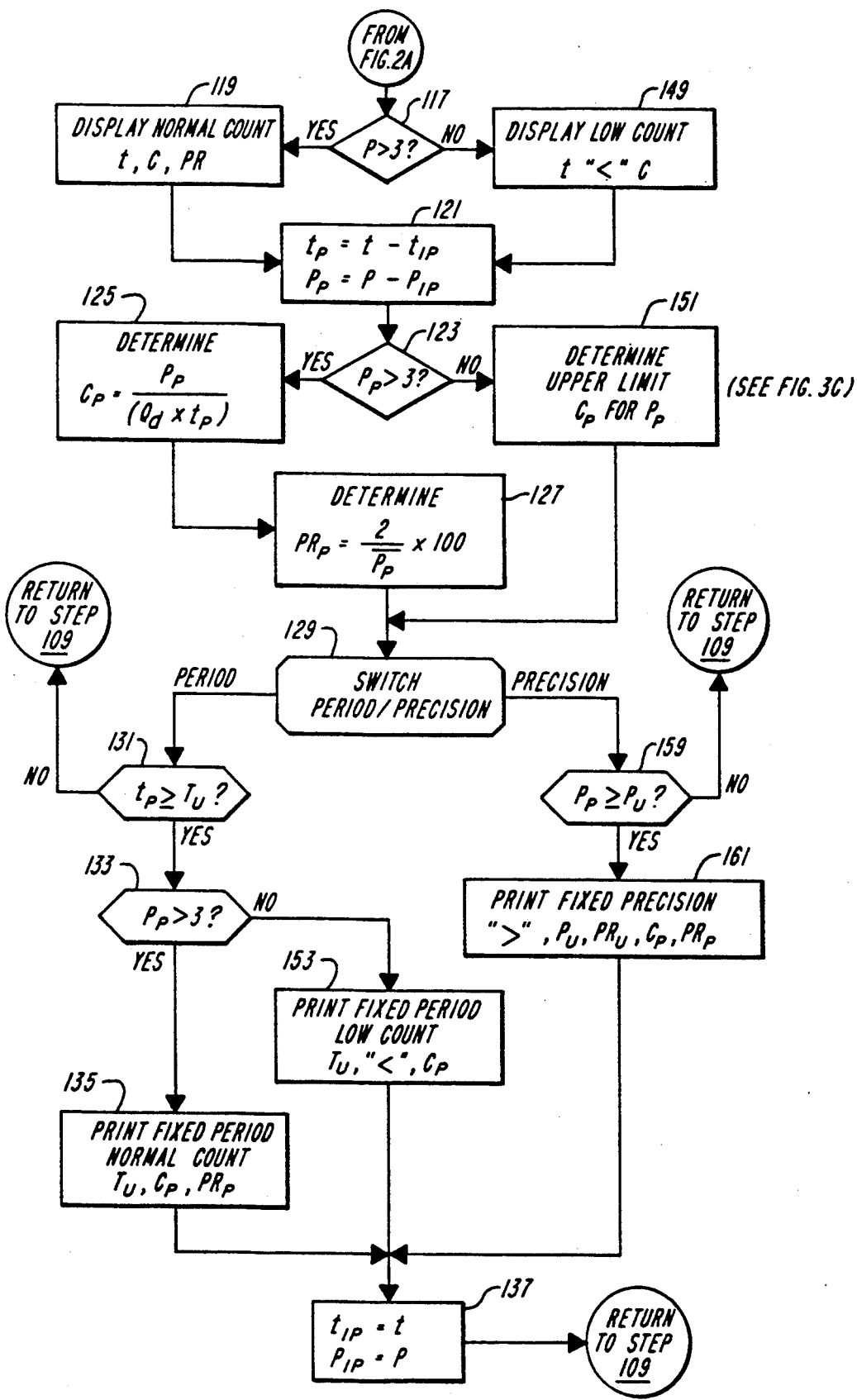
Figure 3C:
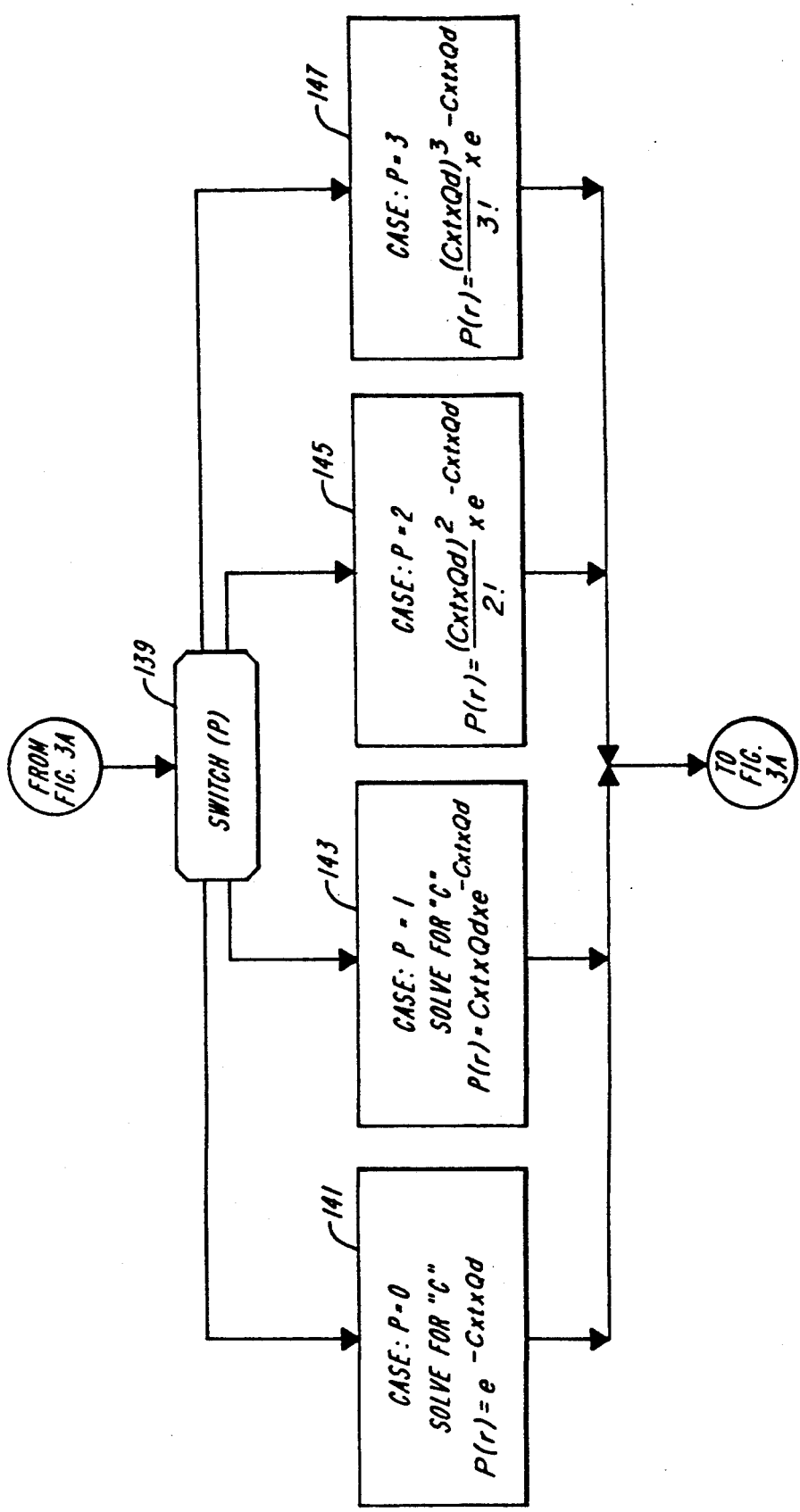

FIGS. 3A-3C is a flow chart illustrating the preferred processing steps used by microprocessor 38 for particle counting, determining particle concentration, and displaying and printing same in a fixed period or fixed precision mode. As will be readily apparent to those skilled in the art, the following disclosure is applicable to the specific field of fiber counting and determining fiber concentration.

Referring to FIG. 3A, the system begins at step 101 wherein certain variables used within the program are initialized. A list and description of the variables used in FIGS. 3A-C is shown below in Table No. 1.

TABLE NO. 1

| Variable Name | Description |
|---|---|
| $T_u$ | User selected fixed time period |
| $PR_u$ | User selected fixed precision |
| $P_u$ | Required particle count for a user selected precision ($PR_u$) |
| t | Total elapsed time |
| p | Total particle count over total elapsed time period (t) |
| $Q_d$ | Flow rate of detected air. |
| C | Time weighted average (TWA) particle concentration) or upper limit concentration) based on a total particle count of (p) and total elapsed time (t) |
| PR | Precision for total particle count (p) |
| $t_{lp}$ | Time of last printout |
| $p_{lp}$ | Total particle count at time of last printout |
| $t_p$ | Time elapsed since last printout ($t-t_{lp}$) |
| $P_p$ | Current particle count since last printout ($p-p_{lp}$) |
| $C_p$ | Current particle concentration (or upper limit particle concentration) since last printout based on the current particle count since last printout ($p_p$), and time elapsed since last printout ($t_p$) |
| $PR_p$ | Precision for current particle count since last printout($p_p$) |
| P(r) | Poisson probability |

After initializing the required variables, the system proceeds to step 103 to prompt the user via LCD screen 40 to select a printout operating mode. If a user has selected the "fixed time period" mode, the system advances to a fixed time period subroutine. Alternatively, if the user selects the "fixed precision" mode the system advances to a fixed precision subroutine.

For the following examples it will be assumed that the flow rate of detected air ($Q_d$) is 10 cc/min ($Q_d=10$).

For a first example, it will be assumed that the user has selected the "fixed time period" mode causing the system to advance to the fixed time period subroutine beginning at step 105. Here, the system prompts the user via LCD screen 40 to select the particular fixed time period (in minutes) for operation. The user then enters the desired time period via keyboard 44 with the value entered assigned to the user selected fixed time period variable ($T_u$). For the first example, it will be assumed that the user has selected a 30 minute sampling time period ($T_u=30$). The system next advances to step 107 where the system starts an internal clock to maintain a total elapsed time value (t). Thereafter, the particle monitor is activated and begins monitoring air samples. The system advances step 109 where the total number of particles detected over elapsed time period (t) is assigned to the total particle count variable (p). The total particle count (p) represents the total number of particle detection signals received via control line 304 from the light detector 12 as described above. In the preferred embodiment, the system continuously displays the total particle count (p) on LCD screen 40.

The program next advances to step 111 where the system checks whether to proceed in a low count mode or a normal count mode based on a threshold particle count value. As will be readily apparent to those skilled in the art, the particular threshold particle count value for switching between a low count and normal count mode can be a constant value set for a particular application or user selectable. A threshold particle count value of 3 is preferred because the associated precision (PR) (at a confidence level of 95%) for any particle count equal to or less than 3 is greater than 100%. Accordingly, the system has been designed to advance to the low count mode when the total particle count is less than or equal to 3 ($p \leq 3$).

Assume for the first example that the total particle count is 100 ($p=100$) and that the total elapsed time value, i.e. the total monitoring time, is 30 minutes ($t=60$). Accordingly, step 1 will cause the system to advance to step 113 to determine the time weighted average (TWA) particle concentration (C) in the normal count mode. Here, the TWA particle concentration (C) is equal to the total particle count (p) divided by the detection flow rate ($Q_d$) multiplied by the total elapsed time period (t). Thus, by equation:

$$C = \frac{p}{(Q_d * t)}$$

Using the values assumed in the first example and a flow rate of 10 cc/min ($Q_d=10$), the TWA particle concentration is: $C=100/(10*60)=0.17$ p/cc.

The system then advances to step 115 where the precision (PR) for the total particle count (p) is determined as twice the standard deviation ($2\sigma$). As is readily apparent to those skilled in the art, the relative standard deviation ($\sigma$) for a series of events, here, particle counts (p), is:

$$\sigma = \frac{1}{\sqrt{p}}$$

which has a statistical confidence of 63%. In an airborne particle monitor, a confidence level of approximately 95% is desired and, therefore, the relative standard deviation ($\sigma$) is insufficient. Accordingly, the precision (PR) at step 115 is set to twice the relative standard deviation ($2\sigma$) which has a known statistical confidence of approximately 95%. Thus, by equation:

$$2\sigma \times 100 = PR = \frac{2}{\sqrt{p}} \times 100$$

The value of $2\sigma$ is multiplied by 100 to indicate precision PR as a percent value. Using the assumed values for the first example, the precision (PR), or sampling error, for a total particle count of 100 ($p=100$) is: $PR=200\sqrt{100}=\pm 20\%$. will be readily apparent to those skilled in the art, the precision can be either a constant value or user selectable. Accordingly, if a higher confidence level is desired, the system can be modified at this step to use $3\sigma$ (99% confidence), $4\sigma$ (99.9% confidence), and so forth.

The system then advances to a routine to display the results of the particle concentration and precision determinations. Referring to FIG. 3B, the system advances to step 117 to again check whether it is in the low count mode or normal count mode. Continuing with the current example ($p=100$), the program will advance to step 9 to display on LCD screen 40 the total elapsed time (t), TWA particle concentration (C), and precision (PR) in the normal count mode. In the preferred embodiment, the system updates the LCD screen 40 with these values once every minute.

The system next advances to step 121 where the time elapsed since last printout ($t_p$) and the current particle count since last printout ($p_p$) is determined. Specifically, the time elapsed since last printout ($t_p$) is equal to the total elapsed time (t) less the time of last printout ($t_p$) (i.e. $t_p = t - t_p$). The current particle count since last printout ($p_p$) is equal to the total particle count (p) less the total particle count at time of last printout ($p_p$) (i.e. $p_p = p - p_p$). Assume for this first example that the last printout occurred at 30 minutes ($t_p = 30$) the total elapsed time is 60 minutes ($t=60$), and the total particle count at time of last printout was 60 ($p_p=60$). Therefore, the time elapsed since last printout is 30 minutes ($t_p = 60-30=30$) and the current particle count since last printout is 40 ($p_p = 100-60=40$).

The system next advances to a routine to determine the current particle concentration ($C_p$), or upper limit particle concentration, since the last printout based on $t_p$ and $p_p$. The routine begins at step 123 where the system checks whether it is in a low count or normal count mode based on the current particle count since last printout ($p_p$). In the first example ($p_p = 40$) the system will advance to step 125 to determine the current particle concentration since last printout ($C_p$) using the normal count concentration equation of step 113 as described above. Using the current assumed values ($t_p=30$, $p_p=40$) the current particle concentration since last printout ($C_p$) is 0.13 p/cc ($C_p=40/(10\times 30)$).

The system then advances to step 127 to determine the associated precision ($PR_p$) for the current particle concentration since last printout ($C_p$) using the precision equation of step 115. Using the current assumed values ($p_p=40$), the precision ($PR_p$) for the current particle concentration since last printout ($C_p$) is 32% ($PR_p = 2\sqrt{40} \times 100 = 32$).

The system next advances to routine to printout the current particle concentration and related precision. Beginning at step 129, the system branches into a fixed time period printout routine or fixed precision printout routine. Continuing with the first example (fixed time period mode), the system will advance to step 131.

Here, the system compares the elapsed time since last printout ($t_p$) to the user selected fixed time period ($T_u$) to check whether a printout is required. If the elapsed time period is not equal to the user selected fixed time period ($t_p < T_u$), the system returns to the particle count step 109 to repeat the process as described. If the elapsed time since last printout is greater than or equal to the selected time period ($t_p \geq T_u$), the system advances to the fixed time period printout subroutine beginning at step 133.

Continuing with the first example ($T_u=30$), the system advances to step 33 and again checks whether it is in the low count or normal count mode base on the current particle count since last printout ($p_p$). For the current example ($p_p=40$), the system advances to print step 35 wherein the current particle concentration ($C_p$) and associated precision ($PR_p$) over the preceding user selected fixed time period $T_u$ is printed on digital printer 42. In the preferred embodiment, the system generates a printout as follows:

| PRINTOUT | DESCRIPTION |
|---|---|
| FIXED PERIOD: | printout mode message |
| 30 min | selected printout period in minutes ($T_u$) |
| 15:33 | time of printout |
| 08 jan 1990 | date of printout |
| 0.13 p/cc | average concentration over last period ($C_p$) |
| +/−32% | precision at 95% confidence ($PR_p$) |

Upon completion of printing, the system then advances to step 137 to update the time of last printout ($t_p$) and total particle count at time of last printout ($p_p$). Thereafter, the system returns to step 109 to repeat the steps as described above absent a user command to terminate monitoring.

Referring back to step 111, if the total particle count is less than or equal to three ($p \leq 3$), the system will advance to the low count subroutine. As discussed above, the threshold value for advancing to the normal and low count modes can be varied for a particular application or user selected. For a second example, it will be assumed that the total particle count (p) is less than or equal to three ($p \leq 3$) advancing the system to the low count subroutine.

Referring to FIG. 3C, the first step 139 of the count subroutine is a switch to branch the system to four different possible cases: zero particles counted (p=0), one particle counted (p=1), two particles counted (p=2), or three particles counted (p=3). The system then uses Poisson statistics to determine an "upper limit" particle concentration for the specific total particle count (p=0, 1, 2, or 3).

Poisson statistics, named after the nineteenth century French mathematician, Siméon Denis Poisson, can be used to determine the probability of a designated number of events occurring when such events occur in a continuum of time or space. Only one value is required to determine the probability of a designated number of events occurring in a Poisson process: the long-run mean number of events under consideration. Thus, Poisson statistics makes it possible to predict the probability of occurrence of 0, 1, 2, 3, or r events where the mean frequency of occurrence of a phenomenon is either known or assumed.

The Poisson formula is as follows:

$$P(r) = \frac{\mu^r e^{-\mu}}{r!}$$

Here, r represents the number of events, P(r) is the Poisson probability that r events have occurred, and $\mu$ is the expected event rate. Accordingly, the probability of discrete events 0, 1, 2, and 3 occurring can be represented by the following terms of the Poisson series:

| Events (r)  | 0          | 1              | 2                  | 3                  |
|-------------|------------|----------------|--------------------|--------------------|
| Probability | $e^{-\mu}$ | $\mu e^{-\mu}$ | $\mu^2 e^{-\mu}/2!$ | $\mu^3 e^{-\mu}/3!$ |

In the present invention, the number of events (r) is the particle count ($p_p$) and the expected rate is equal to $C \times Q_d \times t$, where C is the upper limit particle concentration, $Q_d$ is the detection flow rate, and t is the elapsed sampling time. As stated above, the preferred probability for aerosol monitoring is 95%. Accordingly, the Poisson probability P(r) is equal to $1 - 0.95$ or $0.05$ (P(r)=0.05).

For example, if the system operates for 30 minutes (t=30) at a detection flow rate of 10 cc/min ($Q_d=10$) and has detected zero airborne particles during that period (p=0), the maximum expected airborne particle concentration (i.e. the upper limit airborne particle concentration) can be determined. Using the first term of the Poisson series, $e^{-\mu}$ for zero events, the resulting probability equation can be reduced to: $e^{-C \times 30 \times 10} = e^{-300C} = 0.05$. Accordingly, the upper limit particle concentration (C) is equal to 0.01 p/cc. Therefore, if zero particles are detected after 30 minutes of monitoring there is a 95% probability that the particle concentration is 0.01 p/cc or below. Similarly, the corresponding particle concentration determination for one detection count is performed using the second term of the Poisson series, $\mu e^{-\mu}$, and so forth.

With the above principles in mind, the system's low count subroutine can be explained in detail. Switch 139 determines which term of the Poisson series to be used for the current particle count. When the particle monitor has counted zero particles (p=0) the system is switched to step 141 to determine the upper limit particle concentration (C) for a zero count over the elapsed time period (t). Similarly, the system is switched to step 143 when encountering a single particle count (p=1), step 145 for two particle counts (p=2), or step 147 for three particle counts (p=3).

As will be readily apparent to those skilled in the art, certain variables within the Poisson distribution can be constant for a specific particle monitor and can be used to simplify the determinations performed at steps 141, 143, 145 and 147. Specifically, the detection flow rate ($Q_d$) in the preferred fiber monitor is 10 cc/min ($Q_d=10$) and the desired Poisson probability value P(r) is 0.05. Accordingly, the determination for the upper limit particle concentration (C) for 0, 1, 2, and 3 particle counts can be reduced to 0.3/t, 0.45/t, 0.5818/t, and 0.7076/t respectively.

After determining the associated upper limit particle concentration for a low particle count, the system advances to display the upper limit particle concentration (C). As described above, step 117 determines whether the system will use the low count display or normal count display. For this second example ($p \leq 3$), the system will proceed to step 149 and display the total elapsed time (t) and the upper limit particle concentration (C) (i.e. the system will display the actual particle concentration as being below ("<") C with a 95% probability). As with the normal count display, the system updates the LCD screen 40 with the upper limit particle concentration once every minute.

The system then advances through steps 121 and 123 to update the time elapsed since last printout ($t_p$) and the current particle count since last printout ($p_p$) and to check whether the system is in the low count mode or normal count mode based on the current particle count since last printout as discussed above. Continuing with the second example ($t_p=30$, $p_p \leq 3$), the system will advance to step 151 to determine the current upper limit particle concentration since last printout ($C_p$) based on the current particle count since last printout ($p_p$) and the time elapsed since last printout ($t_p$) using the low count subroutine similar to that illustrated in FIG. 3C.

After determining the upper limit particle concentration since last printout ($C_p$), the system advances to step 129 to switch between the fixed time period or fixed precision printout modes as described above. Continuing with the second example, the system would advance through steps 131 and 133 to print the current upper limit particle concentration since last printout at step 153. In the preferred embodiment, the system generates a printout as follows:

| PRINTOUT | DESCRIPTION |
|---|---|
| FIXED PERIOD: | printout mode message |
| 30 min | selected printout period in minutes ($T_u$) |
| 15:03 | time of printout |

| PRINTOUT | DESCRIPTION |
|---|---|
| | -continued |
| 08 jan 1990 | date of printout |
| <0.01 p/cc | upper limit of expected concentration with 95% probability ($C_p$) |

Upon completion of printing, the system advances through step 37 as described above and then returns to step 109 to continue monitoring the environment absent a user command to terminate same.

Referring back to step 103 for a third example, it will be assumed the system user has selected the fixed precision printout mode. Accordingly, the system will advance to step 155 wherein the user is prompted via LCD screen 40 to select the particular fixed precision for operation (in percent). The user enters via keyboard 44 the desired fixed precision and the value entered is assigned to the variable $PR_u$. For the third example, it will be assumed that the user has selected a fixed precision of 20% ($PR_u=20$). The system next advances to step 157 where the particle count ($P_u$) required for a particle concentration having a precision equal to the user selected fixed precision (at a confidence level of 95%) is determined in advance by the following equation:

$$P_u = \left(\frac{200}{PR_u}\right)^2$$

The required particle count equation is the precision equation of step 117 transposed to solve for a particle count. In the current example, with a selected precision of 20% ($PR_u=20$), the required particle count is equal to 100 ($P_u=(200/20)^2=100$). Thus, the system must detect at least 100 particles to achieve a particle concentration having a precision of ±20% (at a confidence level of 95%)

The system then advances through steps 107 to 129 as described above. In the current example, the system will advance to the fixed precision mode commencing at step 159.

Here, a decision on whether to print the current particle concentration and precision is made. Specifically, if the current particle count since last printout is less than the required particle count ($p_p<P_u$), the system returns to step 109 to continue particle counting. Alternatively, if the current particle count since last printout is less than or equal to the current particle count ($p_p<P_u$) the system advances to step 161 to print the above determinations. In the preferred embodiment, the system generates a printout as follows:

| PRINTOUT | DESCRIPTION |
|---|---|
| FIXED PRECISION: | printout mode message |
| <100f 20% | minimum selected no. of particles and precision |
| 12:49 | time of printout |
| 29 jan 1990 | date of printout |
| 0.21 f/cc | average concentration since last printout |
| +/−20% | precision at 95% confidence |

As will be readily apparent to those skilled in the art, a separate subroutine to print an upper limit particle concentration for a low particle count is not necessary in the fixed precision mode. Once a system user has selected a fixed precision between 1 and 100%, the system, by equation, will not print particle concentrations when the particle count is equal to or less than three ($p≦3$).

Upon completion of printing, the system updates the time of last printout ($t_p$) and the total particle count at time of last printout ($p_p$) at step 137 as described above and returns step 109 to continue monitoring absent a user command to terminate save.

The invention in its broader aspects therefore is not limited to the specific embodiments herein shown and described but departures may be made therefrom within the scope of the accompanying claims without departing from the principles of the invention and without sacrificing its chief advantages.

What is claimed is:

1. A system for determining upper limit airborne particle concentration comprising:
   a sampling means for obtaining an ambient air sample and providing said air sample at a detection flow rate ($Q_d$) to a sensing zone;
   an illumination means at said sensing zone for illuminating any particles present in said air sample;
   a detector means for detecting light scattered by said illuminated particles and producing a particle count signal for each illuminated particle;
   a totaling means for totaling said particle count signals over an elapsed time period (t) and assigning said total to a particle count value (p);
   a determining means for determining an upper limit airborne particle concentration (C) having a Poisson probability (P) by equation:

$$P = \frac{\mu^p \times e^{-\mu}}{p!}$$

where $\mu = C \times t \times Q_d$; and
   an output means for outputting said upper limit airborne particle concentration (C) to an output device.

2. A system for according to claim 1 wherein said Poisson probability (P) has a value of 0.05.

3. The system of claim 1 wherein said determining means determines said upper airborne particle concentration by said equation when said when said particle count value (p) is equal to or less than a threshold particle count;
   when said particle count value p is above said threshold particle count said determining means determines an airborne particle concentration by equation:

$$C = p/(Q_d \times t),$$

said output means outputs said particle concentration to an output device when said particle count value (p) is greater than said threshold particle count value; and
   said output means outputs said upper limit airborne concentration to an output device when said particle count value (p) is equal to or less than said threshold particle count value.

4. The system of claim 3 wherein said threshold particle count value is equal to 3.

5. The system according to claim 3 wherein said elapsed time period (t) is user selectable.

6. The system of claim 3 including said each of said output devices comprises a screen, printer or communication port.

7. The system of claim 3 wherein said totaling means and said determining means comprise a programmable microprocessor.

8. A system for outputting airborne particle concentration having a user selected precision comprising:
   an entry means for entering said user selected precision and assigning said precision to a user selected precision value ($PR_u$);
   a determining means for determining a required particle count ($P_u$) for said user selected precision value ($PR_u$);
   a sampling means for obtaining an ambient air sample and providing said air sample at a detection flow rate ($Q_d$) to a sensing zone;
   an illumination means at said sensing zone for illuminating any particles present in said air sample;
   a detector means for detecting light scattered by said illuminated particles and producing a particle count signal for each illuminated particle;
   a totaling means for totaling said particle-count signals over an elapsed time period (t) and assigning said total to a particle count value (p);
   said determining means determining an airborne particle concentration (C) by equation:

$$C = \frac{p}{(Q_d \times t)}$$

an output means for outputting said airborne particle concentration (C) to an output device when said particle count value (p) is equal to or greater than said required particle count ($P_u$).

9. The system of claim 8 further including a selector means for selecting between a time period mode and a precision mode, and wherein:
   when said selector means is in said time period mode, said entry means enters a user selected time period and assigns said user selected time period to a user selected time period value;
   when said selector means is in said precision mode, said entry means enters said user selected precision and assigns said user selected precision to said user selected precision value;

said determining means determines said required particle count when said selector means in said precision mode;

said output means outputs said particle concentration to an output device when ($\sigma$) said selector means is in said time period mode and said elapsed time period is equal to or greater than said user selected time period value, and (b) said selector means is in said precision mode and said particle count value is equal to or greater than said required particle count.

10. The system of claim 9 wherein:

said determining means determines said airborne particle concentration by said equation when said particle count (p) is greater than a threshold particle count value;

said determining means determines an upper limit airborne particle concentration having a Poisson probability (P) when said particle count value (p) is equal to or less than said threshold particle count value by equation:

$$P = \frac{\mu^p \times e^{-\mu}}{p!}$$

where $\mu = c \times t \times Q_d$;

when said selector means is in said time period mode, said output means outputs said particle concentration when said particle count value (p) is greater than said threshold particle count value, and outputs said upper limit airborne particle count when said particle count value is less than or equal to said threshold particle count value.

11. A method for determining upper limit airborne particle concentration comprising the steps of:

obtaining an ambient air sample and providing said air sample at a detection flow rate ($Q_d$) to a sensing zone;

illuminating at said sensing zone any particles present in said air sample;

detecting light scattered by said illuminated particles and producing a particle count signal for each illuminated particle;

totaling said particle count signals over an elapsed time period (t) and assigning said total to a particle count value (p);

determining an upper limit airborne particle concentration (C) having a Poisson probability ($PR_p$) by equation:

$$P = \frac{\mu^p \times e^{-\mu}}{p!}$$

where $\mu = c \times t \times Q_d$; and outputting said upper limit airborne particle concentration to an output device.

12. The method of claim 11 wherein, when said particle count is equal to or less than a threshold particle value, said upper limit airborne concentration is determined using said formula and is output to said output device; and, when said particle count is greater than said threshold particle value, including the steps of determining an airborne particle concentration by equation:

$$C = p/(Q_d \times t)$$

and outputting said airborne particle concentration to an output device.

13. A method for determining airborne particle concentration having a user selected precision comprising the steps of:

determining said user selected precision and assigning said precision to a value ($PR_u$);

determining a required particle count ($P_u$) for said user selected precision ($PR_u$);

obtaining an ambient air sample and providing said air sample at a detection flow rate ($Q_d$) to a sensing zone;

illuminating at said sensing zone any particles present in said air sample;

detecting light scattered by said illuminated particles and producing a particle count signal for each illuminated particle;

totaling said particle count signals over an elapsed time period (t) and assigning said total to a particle count value (p);

determining an airborne particle concentration (C) when said particle count value (p) is equal to or greater than said required particle count ($P_u$) by equation:

$$C = \frac{p}{(Q_d \times t)}$$

outputting said particle concentration to an output device.

14. The method of claim 13 further including the steps of:
    selecting between a time period mode and a precision mode; entering a user selected time period when in said time period mode and assigning said user selected time period to a user selected time period value;
    entering said user selected precision when in said precision mode;
    determining said required particle count when in said precision mode;
    outputting said particle concentration to an output device when said selector means is in said timer period mode and when said elapsed time period (t) is equal to or greater than said user selected time period value; and,
    outputting said particle concentration to an output device when said selector means is in said precision mode and when said particle count value is equal to or greater than said required particle count.

15. The method of claim 14 including the steps of:
    determining said airborne particle concentration by said formula when said particle count value is greater than a threshold particle count value;
    determining an upper limit airborne particle concentration having a Poisson probability (P) when said particle count is equal to or less than said threshold particle count value by equation:

$$P = \frac{\mu^p \times e^{-\mu}}{p!}$$

where $\mu = c \times t \times Q_d$;
    outputting said particle concentration to said output device when said particle count value is greater than said threshold particle count value; and
    outputting said upper limit airborne particle count to an output device when said particle count value is less than or equal to said threshold particle count value.

* * * * *